United States Patent
Tarpey et al.

(10) Patent No.: US 10,107,720 B2
(45) Date of Patent: Oct. 23, 2018

(54) DETECTION DEVICE AND METHOD OF USING THE SAME

(75) Inventors: Christopher Tarpey, Los Angeles, CA (US); Mary Catherine Parsons, Chula Vista, CA (US); Lijian Gou, Hangzhou (CN); Haipeng Hu, Linan (CN); Fei Gao, Hangzhou (CN); Yinfei Wu, Hangzhou (CN)

(73) Assignee: Alere Switzerland GmbH, Zug (CH)

( * ) Notice: Subject to any disclaimer, the term of this patent is extended or adjusted under 35 U.S.C. 154(b) by 226 days.

(21) Appl. No.: 13/389,433

(22) PCT Filed: Aug. 13, 2010

(86) PCT No.: PCT/CN2010/001227
§ 371 (c)(1),
(2), (4) Date: Apr. 2, 2012

(87) PCT Pub. No.: WO2011/017911
PCT Pub. Date: Feb. 17, 2011

(65) Prior Publication Data
US 2012/0276653 A1    Nov. 1, 2012

(30) Foreign Application Priority Data

Aug. 13, 2009 (CN) .......................... 2009 1 0102113
Aug. 13, 2009 (CN) ..................... 2009 2 0191917 U
Aug. 13, 2009 (CN) ..................... 2009 2 0191918 U

(51) Int. Cl.
*G01N 21/00* (2006.01)
*G01N 1/10* (2006.01)
*G01N 33/493* (2006.01)
*G01N 1/02* (2006.01)
*G01N 33/487* (2006.01)

(52) U.S. Cl.
CPC ............. *G01N 1/10* (2013.01); *G01N 33/493* (2013.01); *G01N 33/4875* (2013.01); *G01N 2001/022* (2013.01); *G01N 2001/027* (2013.01)

(58) Field of Classification Search
None
See application file for complete search history.

(56) References Cited

U.S. PATENT DOCUMENTS

| 6,616,893 | B1 | 9/2003 | Pham |
| 2005/0032234 | A1 | 2/2005 | Ramsey |
| 2008/0260581 | A1* | 10/2008 | Rosman ................ B01L 3/5029 422/68.1 |

FOREIGN PATENT DOCUMENTS

| CN | 2513939 Y | 10/2002 |
| CN | 201159737 Y | 12/2008 |
| CN | 201212889 Y | 3/2009 |
| CN | 201397740 U | 6/2010 |

OTHER PUBLICATIONS

Georgia Tech, 2007, retrieved from internet: http://usability.gtri.gatech.edu/products/bottles/bottle_components.php.*

* cited by examiner

*Primary Examiner* — Xiaoyun R Xu
(74) *Attorney, Agent, or Firm* — DLA Piper LLP (US)

(57) ABSTRACT

A detection device (100) comprises a detecting chamber (32) containing a detecting element for analyzing whether a specimen containing an analyte, and an indicating element (8) displaying whether the detection is activated. The method for using the detection device (100) is also disclosed.

15 Claims, 5 Drawing Sheets

DETECTION DEVICE AND METHOD OF USING THE SAME

CROSS REFERENCE TO RELATED APPLICATIONS

This application is a 35 USC § 371 National Stage application of International Application No. PCT/CN2010/001227 filed Aug. 13, 2010, now pending; which claims the benefit under 35 USC § 119(a) to China Patent Application No. CN200920191918.3 filed Aug. 13, 2009, China Patent Application No. CN200910102113.1 filed Aug. 13, 2009 and China Patent Application No. CN200920191917.9 filed Aug. 13, 2009. The disclosure of each of the prior applications is considered part of and is incorporated by reference in the disclosure of this application.

TECHNICAL FIELD

The present invention relates generally to a detection device. More specifically, it relates a detection device for detecting illegal drugs.

BACKGROUND

Illegal drugs are easily accessible to ordinary people these days, and their uses are seen more frequently. To ensure safety environments in works and fair competitions in sports, more and more often collection and detection devices for detecting illegal drugs in body fluids have to be used by non-professionals at ordinary places. Traditional collection and detection devices, however, cannot quantify the specimen accurately and, therefore, cannot satisfy the requirements for accurate quantification or micro-operation.

U.S. Pat. No. 6,372,515 discloses a specimen collection and detection device, which comprises a urine specimen cup for collecting urine specimen, and a test card having a plurality of test strips for detecting the urine specimen. When in use, the test card is inserted into the urine specimen cup such that the test strips are in contact with the urine specimen, and the test can be completed in a few minutes in this way. After completion of the test, the urine specimen in the cup is already contaminated by materials in the test reagent strips and cannot be used for a second confirmation carried out by professionals.

ZL200420107950.6 also discloses a body fluid specimen detection device, which achieves the purpose of quantifying detection by having a piston hole having one end opened being disposed at the bottom of the cup, a through hole communicating with the collection chamber, and a through hole communicating with a slot for transferring liquid specimen. This published utility model comprises a first through hole and a second through hole. However, such a manner may trap gas bubble and specimen in an annular slot inside the piston hole during operation, resulting in errors in quantified detection and thereby producing inaccurate results.

ZL200720303101.1 discloses yet another liquid specimen collection and detection device, which comprises a collecting chamber, a detecting chamber, and a transferring chamber; the transferring chamber is connected with the collecting chamber and the detecting chamber, respectively, through at least two through holes, wherein at least one of the through holes has both ends of the opening opened at two sides of either the highest or the lowest point of the transferring chamber. This invention changes positions of through holes in a liquid specimen detection device and thereby solves the technical problem of having gas bubble generated from excessive flowing speed of liquid specimen in ordinary detection devices, thereby blocking liquid specimen flowing and causing insufficient amount of specimen for detection.

SUMMARY OF THE INVENTION

The present invention relates to a detection device, which comprises a detecting chamber containing a detecting element analyzing whether a specimen containing an analyte, and an indicating element for displaying whether the detection is activated. Preferably, the detecting chamber further comprises a support element for supporting the detecting element. The indicating element, on the one hand, is mainly for displaying whether the detecting element has been used: in circumstance that a liquid specimen is present, the indicating element's indicating that the detecting element has been used suggests that the detection is activated. On the other hand, if the indicating element indicates that the detection is already activated prior to detecting, it means that the detection device has been operated incorrectly, and such a detection device and its detecting element are therefore deemed used and cannot be used for detection any more.

Preferably, the detection device further comprises a transferring chamber for transferring liquid specimen to the detecting chamber. More preferably, the detection device further comprises a collecting chamber for collecting liquid specimen, and the collecting chamber is connected with the detecting chamber through the transferring chamber. Transferring liquid specimen in such a detection device having a transferring chamber can be achieved by changing the position of the transferring chamber. In a specific example, the transferring chamber comprises a piston chamber having a piston, and the piston chamber and the piston form an opened annular slot for transferring the liquid specimen and a closed annular slot for disposing the indicating element, while changing the position of the transferring chamber can be achieved through a driving element.

If the liquid specimen in the transferring chamber has been transferred to the detecting chamber, information can be obtained from the indicating element that the detection is activated. At this time, the liquid specimen contacts with the detection reagent strips in the detecting chamber and the detection reaction is activated. Preferably, the indicating element moves together with the transferring chamber. In this manner, change of the position of the transferring chamber can be observed directly, which indicates whether the detection has been activated. The indicating element can be a self-adhesive tape. More preferably, the detection device further comprises an observation window for observing the indicating element and obtaining the signal of whether the detection is activated.

In addition, the present invention also relates to a driving element, which activates liquid flowing from the transferring chamber to the detecting chamber. Such activation can be irreversible. The driving element can further comprise a blocking element connected with the driving element as one piece before the detection is activated. The blocking element prevents the driving element from having inadvertent movement before the detection is activated, such as movements during production, assembly, transportation, specimen collection and the like. If without the provisional "protection" by the blocking element and if inadvertent movement occurs, the detection could not be further carried out and prompt detection of specimen would therefore not be achieved. Additionally preferable, the blocking element that is connected with the driving element before the detection is activated can be peeled off from the driving element prior to activating the detection. More preferably, the blocking element has a handle to facilitate its peeling off from the driving element. In one specific example, the transferring chamber comprises a piston chamber having a piston, with the driving element being disposed at one end of the piston, and the blocking element covering outside of the piston; when the detection is not activated, the driving element and the blocking element are connected as one piece, and when the detection is activated, the blocking element and the driving element are separated.

The present invention also relates to a method of using a detection device, such a detection device has a detecting chamber containing a detecting element analyzing whether a specimen containing an analyte, and an indicating element for displaying whether the detection is activated, and the method comprises: collecting liquid specimen, determining whether the detection is activated by observing an indicating element, and conducting the detection. Preferably, the detection device can further comprise a transferring chamber for transferring liquid specimen to a detection chamber, and the indicating element is located in the transferring chamber and moves together with the transferring chamber. And the method of using such a detection device can comprise: collecting liquid specimen; moving the transferring chamber such that the liquid specimen can flow from the transferring chamber to the detection chamber, wherein the indicating element also moves together with the transferring chamber; observing the indicating element to determine whether the detection is activated, and conducting detection. Even more preferably, the transferring chamber of the detection device can contain a piston chamber having a piston, the piston chamber and piston form an opened annular slot for transferring liquid specimen and a closed annular slot for disposing the indicating element; further, the detection device further contains an observation window for observing the indicating element. The method of using the detection device, then, comprises: collecting liquid specimen; moving the transferring chamber such that the liquid specimen can flow from the transferring chamber to the detection chamber, wherein the indicating element moves together with the transferring chamber; observing the indicating element from the observation window to determine whether the detection is activated, and conducting detection.

The present invention has the beneficial effect of displaying a signal when the detection is activated, which can facilitate detection counting and determination. In addition, the present invention can prevent position change of the transferring chamber, and can be easily operated when the detection is activated.

Figure 1:
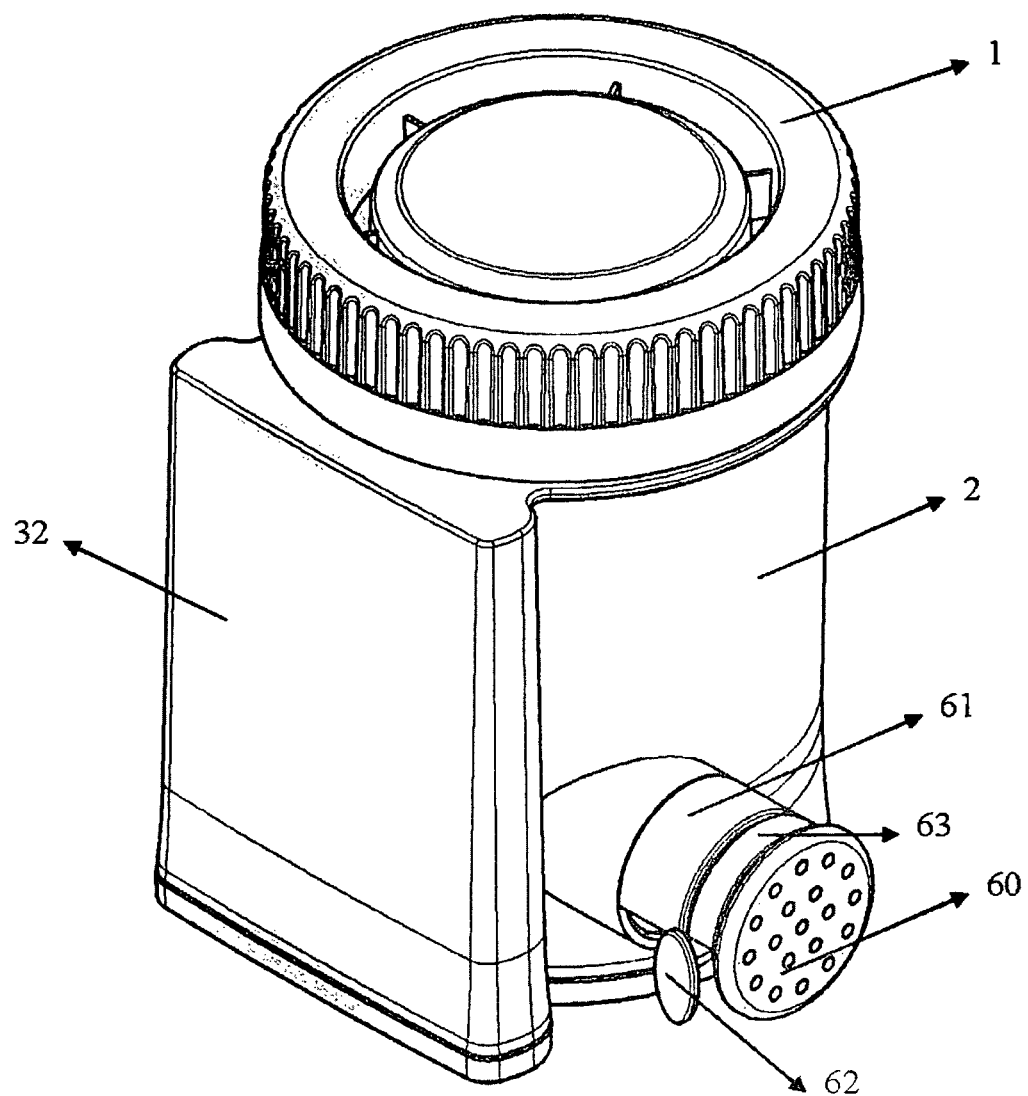
FIG. 1 is an outside view of a specific example of the invention.

Remarks of the reference signs: detection device (a cup for collecting and detecting urine specimen) 100, cup lid 1, cup body 2, cup mouth 20, cup mouth screw 201, collecting chamber 21, piston chamber (transferring chamber) 22, piston 23, rubber band 24, opening of piston chamber 25, opened annular slot 26, upper through hole 27, lower through hole 28, cup seat 3, absorbent paper 31, detecting chamber 32, supporting bar 33, slot 34, seal ring 4, test card (detection card) 5, detection result displaying region 51, detection reagent strip 52, plugboard 53, through hole on the plugboard 54, window of self-adhesive film 55, plugboard protrusion 56, driving element 6, driving handle 60, blocking element 61, 63, handle 62, closed annular slot 7, indicating element 8.

DETAIL DESCRIPTION OF THE INVENTION

Definitions

Unless defined otherwise, all technical and scientific terms used herein have the same meaning as commonly understood by skilled artisans in the art to which the present invention belongs. Generally, the nomenclature used herein and the manufacture or laboratory procedures described below are well known and commonly employed in the art. Throughout the description, where a term is provided in the singular, the inventors also contemplate the plural of the term unless otherwise indicated; further, the following terms, unless otherwise indicated, shall be understood to have the following meanings:

"Detect" or "analyze" denotes assaying or testing whether a substance or a material presents in a sample or specimen. Such a substance or material includes (but not limited to) a chemical substance, an organic compound, an inorganic compound, a metabolite, a drug or a metabolite thereof, an organic tissue or a metabolite thereof, a nucleic acid, a protein, and a combination thereof. Further, "detect" or "analyze" denotes measuring the amount of a substance or a material. In addition, assay here also includes immune assay, chemical assay, enzyme assay and the like.

"Specimen" of the present invention refers to substances that may contain an interested analyte and can be used for detecting, testing or assaying the presences of such an analyte. Specimen can be fluid or liquid, which are all described as liquid specimen here, and include blood, plasma, serum, urine, saliva, various secretions, and liquid solutions or fluids formed by pre-treating solid and semi-solid specimen. Methods including immune assay, chemical assay, enzyme assay and the like can be used to detect whether the collected specimen contains the interested analyte.

The device and method of the present invention can be used to detect or analyze any "analyte." Examples of analyte that can be detected or analyzed by the device and method of the present invention include (but not limited to) human chorionic gonadotropin (hCG), Luteinizing Hormone (LH), follicle stimulating hormone (FSH), Hepatitis C Virus (HCV), Hepatitis B Virus (HBV), Hepatitis B Virus Surface Antigen, AIDs virus, and any drugs of abuse. Analyte can be detected in any liquid or liquefied specimen, such as urine, saliva, blood, plasma, or serum. Other examples of analyte include creatinine, bilirubin, nitrite, protein (non-specific), blood, white cell, blood sugar, heavy metal and toxin, cell components (such as specific proteins and sugars of specific types of cells), and any other analyte suitable for the form of lateral flow test.

Analyte can also be some semi-antigen substances including drugs (such as drugs of abuse). "Drugs of abuse" (DOA) refers to using drugs not for medical purpose (typically for paralyzing nerves). Abuse of these drugs would damage the body and nerves, causing dependency, addiction and/or death. Examples of drugs of abuse include cocain, amphetamine (such as black beauty (biphetamine), white amphetamine tablet, dextroamphetamine, dextro-benzedrine, Beans); methamphetamine (crank, methamphetamine, crystal, speed); barbiturate (such as Valium, Roche Pharmaceuticals, Nutley, N.J.); ataractic (drugs for assisting sleeping); lysergic acid diethylamide (LSD); depressor (downers, goofballs, barbs, blue devils, yellow jackets, methaqualone); tricyclic antidepressants (TCA, i.e., imipramine, amitriptyline and doxepin); phencyclidine (PCP), tetrahydrocannabinol (THC, pot, dope, hash, weed, and etc); opiates (i.e., morphia, opium, codeine, heroin, oxycodone); antianxiety drug and sedative-hypnotic drugs; antianxiety drug is mainly for reducing anxiety, tension, fears and for stabilizing emotion as well as sedative-hypnotic, including benzodiazepines (BZs), non-typical BZs, fused-dinitrogen-NB23Cs, benzepins, ligands of BZ acceptors, ring-opening BZs, diphenylmethane derivatives, piperazinecarboxylates, piperidinecarboxylates, quinazoline ketones, thiazine and thiazole derivatives, other heterocyclics, sedative/anodyne of imidazole type, propylene glycol derivatives-carbamates, aliphatic compounds, and anthracene derivatives. The device can also be used to detect drugs which is for medical purpose but is easily overdose such as tricyclic antidepressants (imipramine or analogs) and acetaminophen. These drugs will be decomposed to different small molecules after absorbed by human body, and the small molecules are present in body fluids such as blood, urine, saliva, and perspiration.

Detection Device

The detection device 100 in the present invention comprises a detecting chamber 32 for containing a detecting element 5 for analyzing whether an analyte is present in the specimen. The detection device 100 can be made of various materials having different shapes, such as plastics of various specifications.

In a specific example, the detection device 100 further comprises an indicating element 8 for displaying whether the detection is activated. The indicating element 8 is mainly used, on the one hand, for displaying whether the detecting element 5 has been used; if the indicating element 8 displays that the detecting element 5 has been used when liquid specimen is present, then it indicates that the detection has been activated. On the other hand, if the indicating element 8 displays that the detection is activated before detection, it means that the detection device 100 has been operated incorrectly, such a detection device 100 and the detecting element 5 are deemed used and the detection activated as well, and cannot be used for detecting any more. The detection is regarded as activated if the detecting element 5 or the detection device 100 has been used. A signal that detection has been activated can be a signal formed by the indicating element 8 per se, and can also be that formed by the reaction of the indicating element 8 with other substances. The indicating element 8 comprises chemical indication, such as showing colors. In one specific example, it can show a color of dark red through a reaction of chemical substances, such as the reaction between potassium thiocyanate and ferric ions. In another example, the indicating element can comprise using edible colorant. In yet another example, the indicating element 8 can comprise a pH agent. A material having a pH agent, such as pH paper, can be used in the indication region of the indicating element. Different liquid specimens have different pH, for example, urine has a pH between 5 and 7. After contacting the specimen, the color of the pH paper on the indication region can change from yellow to grass green, thereby achieving the purpose of indicating. Further, indication also includes physical indications. In one example, the indicating element 8 can be a colored material having at least a portion covered by an essentially opaque layer. When liquid is present, the opaque layer becomes transparent such that the colored material can be observed. In another example, the indicating element 8 can be a colored self-adhesive tape, the self-adhesive tape cannot be seen or is hided before detection, and can be seen clearly after the detection is activated. Preferably, the detection device 100 further comprises a collecting chamber 21 for collecting liquid specimen, and a transferring chamber 22 for transferring liquid specimen from the collecting chamber 21 to the detecting chamber 32. The indicating element 8 can be disposed at any place of the detection device, such as on the collecting chamber 21, transferring chamber 22 or detecting chamber 32. More preferably, the indicating element 8 can be on the transferring chamber 22 since the transferring chamber 22 is a key to activate the detection. In a specific example, the indicating element 8 is disposed on the transferring chamber 22 and changes the position when the position of the transferring 22 changes. Specifically, after specimen collecting, the liquid specimen is stored in the collecting chamber 21 and the transferring chamber 22. At this time, the transferring chamber 22 can be driven to move such that liquid specimen in the transferring chamber enters the detecting chamber 32, wherein detecting element 5 presents. A specimen absorbing part of the detecting element 5 can detect the liquid specimen in the detecting chamber 32, therefore initiating detection. If liquid specimen enters the detecting chamber 32, it can be determined promptly that the detecting in the detecting chamber 32 starts. Therefore, the indicating element 8 so configured also indicates whether detection is activated when indicating whether liquid sample transfers from the transferring chamber 22 to the detecting chamber 32. Preferably, the transferring chamber 22 includes a piston chamber having a piston 23, the piston 23 and the piston chamber can form several annular slots. Liquid specimen can be temperately stored and transferred in an opened annular slot 26 of the transferring chamber 22, while the indicating element 8 is disposed in the closed annular slot 7. When the opened annular slot 26 of the transferring chamber 22 is pushed towards the closed end of the piston 23 by the driving element 6, the closed annular slot 7 also moves towards the closed end of the piston 23. When the opened annular slot 26 and the detecting chamber 32 are in direct fluid communication and thereby allowing the liquid specimen stored in the open annular slot 26 enters the detecting chamber, the indicating element 8 is at a position that can send a signal that the detection is activated.

More preferably, the detection device 100 further comprises an observation window 54 for observing a signal displayed by the indicating element. The observation window 54 can be on the collecting chamber of the detecting device, or on the transferring chamber 22, the detecting chamber 32, or even other places. The observation window 54 on the detecting device can be transparent from which the signal indicating that the detection is activated can be seen clearly. For example, a transparent detecting chamber or transferring chamber can be used as an observation window themselves. Preferably, an observation window 54 can be a through hole on the test card 5 of the detecting chamber. Typically, a detection device 100 is a plastic product; a test card 5 can be designed to have a shape of the white plugboard 53 on which a through hole 54 is provided. Through the through hole 54, a signal indicating that the detection is started, which is displayed from the indicating element 8 in the transferring chamber, can be seen. More preferably, the indicating element 8 is at a first position before the detection is activated. After the driving element 6 pushes the transferring chamber 22 such that the liquid specimen in the transferring chamber 22 flows into the detecting chamber 32, the indicating element 8 is at a second position that is right behind the detection window 54, i.e., the through hole 54 on the detecting card, then the operator of the detection device can clearly see the indicating element 8 and receive the signal that the detection is activated through the window 55.

In another specific example, the detection device 100 includes a driving element 6. The detecting element 5 in the detecting chamber 32 can not be operated automatically and needs to be activated by an action, and the driving element 6 can be used to activate the detection of the detecting chamber 32. By pushing the driving element 6 or other actions, the liquid specimen enters the detecting chamber 32 and activates reaction of the detecting element 5. The detection device 100 also includes a collecting chamber 21 to collect liquid specimen, and a transferring chamber 22 connecting the collecting chamber 21 and the detecting chamber 32. The driving element 6 is to flow the liquid specimen from the transferring chamber to the detecting chamber and to activate the detection reaction. The driving element 6 is preferably located at a position to be used cooperatively with the transferring chamber 22. In a specific example, the driving element 6 can be on the cup lid 1. When needed, it can be taken away from the cup lid 1, and can be used to drive the transferring chamber 22 from one end to another end, thereby transferring the liquid specimen in the transferring chamber 22. Preferably, the driving element 6 is associated with the transferring chamber 22. When in use, it can directly drive the transferring chamber so as to facilitate the operation. More preferably, the driving element 6 further comprises blocking element 61, 62, 63. The blocking element 61, 62, 63 is for preventing the driving element 6 from having inadvertent movement. Specifically, the blocking element 61, 62, 63 prohibits the action of the driving element 6 when liquid transferring is not desired. When liquid specimen needs to be transferred, the blocking element 61, 62, 63 can be released such that the driving element 6 can be in action. In one preferable example, the blocking element 61, 62, 63 and the driving element 6 are connected together as one piece. To be more specific, the blocking element 61, 62, 63 and the driving part 6 is connected together as one piece before the detection is activated, and the blocking element 61, 62, 63 can be peeled off from the driving element 6 when it needs to activate the detection, then the driving element 6 can play the role of driving the transferring chamber 22. In a more preferably example, transferring chamber 22 comprises a piston chamber, a piston 23 is included inside the piston chamber 22, and the blocking element 61, 62, 63 is covered outside the piston 23, and the driving element 6 is placed at one end of the piston 23. Removing the blocking element 61, 62, 63 from the outside of the piston 23, then the driving element 6 can be driven forward without limitation from the blocking element 61, 62, 63. The movement of the piston drives the liquid from the transferring chamber 22 to the detecting chamber 32, thus activating the detection. Further preferably, the blocking element 61, 62, 63 can further include a handle 62 that can be easily held. By using the handle 62, the blocking element 61, 62, 63 can be peeled off very easily from the driving part 6.

In the above preferences, the detection device 100 can further comprise a collecting chamber 21 for collecting liquid specimen, a detecting chamber 32 that contains a test card 5, and a transferring chamber 22 that transfers liquid specimen for the collecting chamber 21 to the detecting chamber 32.

The chamber of the collecting chamber 21 can be in any form such as cylinder, an injector, a chimney, or any other shapes capable of storing liquid. The collecting chamber 21 consists of cup body 2, cup mouth 20 and cup lid 1. Cup mouth 20 and cup lid 1 can be sealed to ensure that liquid is stored in the cup body 2 without leaking. Cup mouth 20 and cup lid 1 can be sealed by various manners, such as that the cup body 20 and cup lid 1 have screw thread 20 for matching with one another and to achieve the purpose of sealing by turning. More preferably, a sealing ring 4 can be provided inside of the cup lid 1, the device is sealed through pressing the sealing ring 4 against the edge of the cup mouth 20.

The detecting chamber 32 may include cup seat 3 and the test card 5. The cup seat 3 is to support the entire detection device. The bottom of the cup seat 3 can further comprise water absorbing material 31 and a slot 34, and the water absorbing material 31 is used to absorb redundant liquid in the slot 34 such that the liquid does not leak from the cup seat 3 to contaminate environment. The detecting element 5 can be inserted inside the slot 34 for detecting whether there is an analyte contained in the liquid specimen. A support bar 33 is also contained inside the slot 34 for supporting the plugboard protrusion 56 on the test cart 5 such that the test card 5 having detection strips can partially hang above the slot 34 of the cup seat. The benefit of this configuration is that the detection reagent strip 52 is always extendingly hanged when the detection reagent strip 52 absorbs the liquid specimen, thereby not allowing the detection result be affected by bending of the detecting reagent strip 52. The detecting element 5 can be a lateral flow test reagent paper 52, and can also be a plugboard 53 having several detection reagent strips. Various detecting elements can be combined together and used in the present invention. For example, detection reagent paper and detection reagents, such as molecules specifically bond to analyte and fixed on the detection region, can be used. These detection reagent strips and detection reagents are all conventional testing means well known to the ordinary persons skilled in the art.

The transferring chamber 22 is between the collecting chamber 21 and the detecting chamber 32 and can transfer the liquid specimen from one chamber to another chamber. The transferring chamber 22 and the collecting chamber 21 or detecting chamber 32 can be next to each other, even share same walls. The transferring chamber 22 can be a controlled opening, when the opening is open, liquid flows from one chamber to another chamber through the opening. The transferring chamber 22 can also be a bi-directional valve, rotating the valve allows liquid between two chambers to communicate. The transferring chamber 22 can also be a piston chamber having a piston 23, and the liquid in the collecting chamber 21 can be transferred to the detecting chamber 32 by changing the position of the piston 23. The benefit of such a transferring chamber 22 is that the liquid specimen flows only at one direction, and the liquid specimen that has been detected and contaminated by the detection reagents in the detecting chamber 32 cannot enter the collecting chamber 21, which means that the liquid specimen in the collecting chamber 21 cannot be contaminated and can be used for second test or detection. The transferring chamber 22 can further comprise some through holes. For example, the transferring chamber can have a upper through hole 27 connected with the collecting chamber 21, and a lower through hole 28 connected with the detecting chamber 32. More preferably, when the upper through hole 27 is connected with the collecting chamber 21, the transferring chamber 22 and the collecting chamber 21 are in direct fluid communication, while the transferring chamber 22 and the detecting chamber 32 are not in fluid communication. Likewise, when the transferring chamber 22 is connected with the detecting chamber 32 via the lower through hole 28 and is in fluid communication, the transferring chamber 22 and the collecting chamber 21 are not in fluid communication. Such a design facilitates the liquid transferring between the collecting chamber 21 and the detecting chamber 32 without causing free flowing of liquid between the collecting chamber 21 and the detecting chamber 32. A piston 23 can be provided inside the transferring chamber 22, and the piston 23 and the piston chamber 22 are connected with glide sealing. The piston 23 can also have a hollow slot connected with the collecting chamber 21 via the upper through hole 27, or with the detecting chamber 32 via the lower through hole 28. The upper through hole 27 and the lower through hole 28 cannot be connected with the hollow slot simultaneously. The hollow slot can be in shapes of a ring, a square, or other regular or irregular shapes. The location of the piston 23 in the piston chamber 22 can be changed by fingers of an operator or other tools, such as the driving element to achieve the purpose of transferring the liquid specimen. In the transferring chamber 22, piston 23, piston chamber 22 and the rubber band 24 can form several annular slots, such as the opened annular slot 26 and the closed annular slot 7 for transferring the specimen. Taking the opened annular slot 26 as an example, when at the initial state, the opened annular slot 26 communicates with the collecting chamber 21 by means of the upper through hole 27, when the collecting chamber 21 contains liquid specimen, the liquid can enter the opened annular slot 26 via the upper through hole 27. Moving the piston 23 such that the opened annular slot 26 is not connected with the upper through hole 27 any more, but is in communication with the lower through hole 28, the liquid in the opened annular slot 26 then can flow into the detecting chamber 32 via the lower through hole 28, thereby initiating the detection reaction to detect whether the liquid specimen contains the analyte. In particular, the present invention can also quantify the transferred liquid specimen through adjusting and maintaining the size of the opened annular slot 26.

The present invention also relates to a method of using the detection device 100, which comprises: collecting liquid specimen; observing the indicating element 8 and determining whether the detecting is activated; and conducting detection. Preferably, the detection device 100 further comprises a transferring chamber 22 that transfers liquid specimen to the detecting chamber 32, the indicating element 8 is disposed in the transferring chamber 22 and moves together with the transferring chamber 22. The method therefore comprises: collecting liquid specimen; driving the transferring chamber 22 such that the liquid specimen flows from the transferring chamber 22 to the detecting chamber 32, wherein the indicating element 8 moves together with the transferring chamber 22; observing the indicating element 8 and determining whether the detecting is activated; and conducting detection. More preferably, the detection device 100 further comprises an observation window 54 for observing the indicating element that shows whether the detection is activated. Accordingly, the method of using the detection device 100 comprises: collecting liquid specimen; driving the transferring chamber 22 such that the liquid specimen flows from the transferring chamber 22 to the detecting chamber 32, wherein the indicating element 8 moves together with the transferring chamber 22; observing the location of the indicating element 8 and determining the detection is activated from the observation window 54; and conducting detection.

The following is detailed explanation of examples of the present invention in combination with the specific figures. These specific examples are only exemplifications without limiting the spirit of the present invention, other specific examples generated from combining the prior art and the present invention by a person skilled in the art are not excluded.

Example 1

Figure 2:
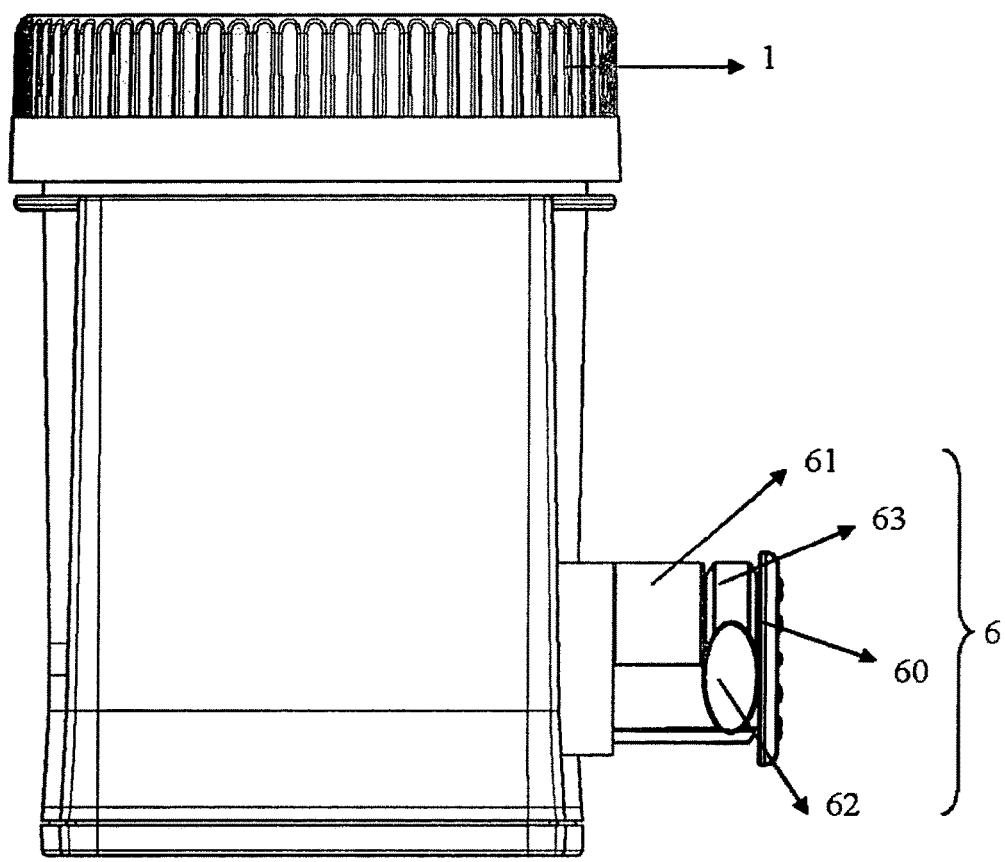
FIG. 2 is a frontal view of a specific example of the invention.
Figure 3:
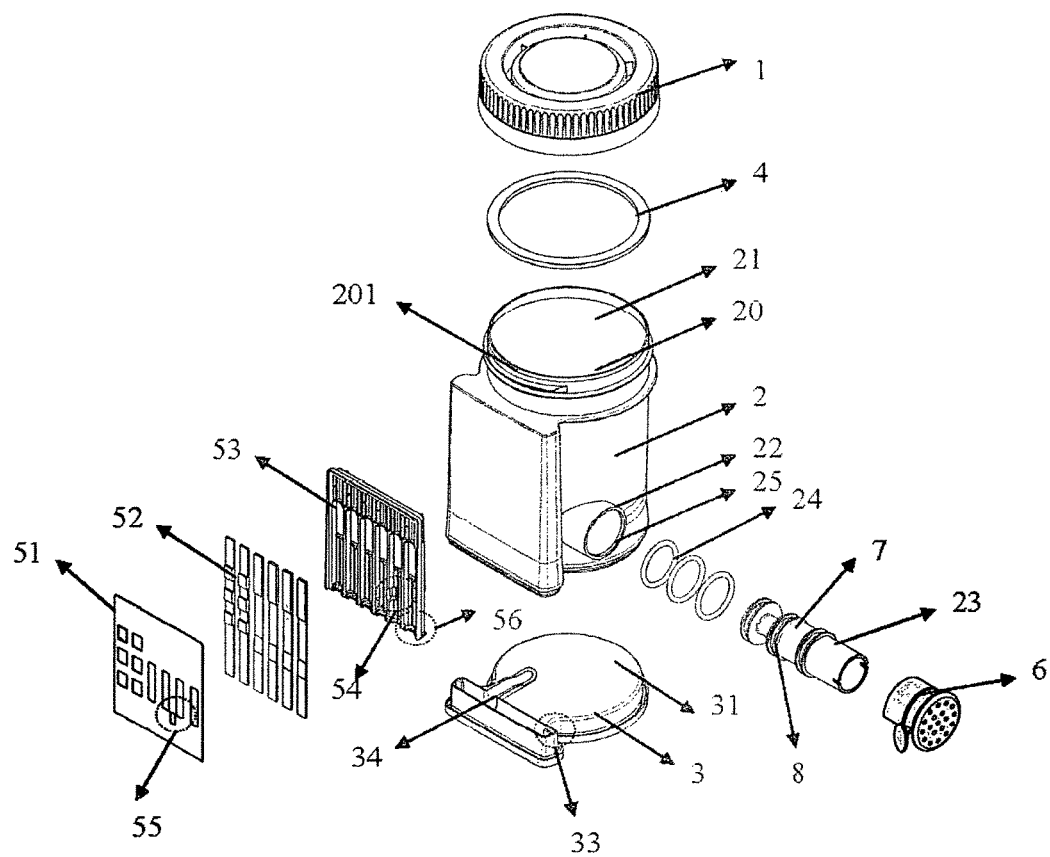
FIG. 3 is an exploded view of a specific example of the invention.

As illustrated in FIGS. 1, 2 and 3, the detection device 100 comprises the collecting chamber 21 and the detecting chamber 32, and the piston chamber (transferring chamber) 22 that transfers the liquid in the collecting chamber 21 to the detecting chamber 32. The collecting chamber 21 includes the cup body 2 that has a cup mouth 20 at the top and a cup chamber inside; the cup mouth 20 has a cup lid 1, the cup lid 1 and the cup mouth 20 have cross sections of round shape, and the cup 1 is connected with the cup mouth 20 through the screw thread 201 of the latter. The bottom of the detecting chamber 32 has a cup seat 3 provided with a socket 34 having two support bars 33 inside for supporting the protrusion 56 on the plugboard such that the test card 5 having testing strips can partially hang over the socket 34 of the cup seat. The benefit of this configuration is that the detection reagent strip 52 can maintain a perpendicularly hanging status during the process that the detection strip absorbs liquid specimen, thereby not allowing the detection result be affected by bending of the detection reagent strip 52. The piston chamber 22 communicates with the cup body through the upper through hole 27 on the upper wall, and with the slot 34 through the lower through hole 28 on the lower wall: there is a transverse branch slot at the cup seat 3, which extends from the slot 34 and ends right under the lower through hole 28, and the lower through hole 28 communicates with the slot 34 via this transverse slot. There is a piston 23 inside the piston chamber 22, glidingly sealing with the piston chamber. The piston 23 also has an opened annular slot 26. When the piston 23 is in the first position, the opened annular slot 26 is connected with the collecting chamber by means of the upper through hole 27 but is separated from the detecting chamber, and forms a hollow chamber for containing liquid specimen enters from the cup chamber. There is a rubber band 24 on the piston 23. When at the second position, the opened annular slot 26 is separated from the cup chamber but is connected with the slot 34 by means of the lower through hole 28. The upper through hole 27 and the lower through hole 28 cannot communicate with the opened annular slot 26 simultaneously. The upper through hole 27 and the lower through hole 28 are strap-like openings having a shape of arc surrounding the vertical axes of the piston 23, with both openings having an arc central angle of 100 degree. The upper through hole 27 is located at the highest position 7 of the piston chamber, with one end of the opening ending at the interface of the piston chamber 22 and the inner wall of the cup body 2 and the other ending at a place where the transferring chamber 22 is protruded over the inner wall of the cup body 2. The lower through hole 28 is located at the lowest position 8 of the piston hole 22, with one end of the opening ending at the interface of the piston chamber 22 and the inner wall of the cup body 2 and the other ending at a place where the piston chamber 22 is protruded over the inner wall of the detecting chamber 32. The upper through hole 27 and the lower through hole 28 are not on the same plane. One end of the piston 23 is provided with a driving element 6 comprising a driving handle 60 and two blocking loops 61, 63, and a handle 62 between the two blocking loops. The connection between the blocking loops 61 and 63 and between the blocking loop 63 and the driving handle 60 can be peeled off easily, which is to tear off the blocking loop 63 from the driving handle 60 via the handle 62. In addition, a layer of green self-adhesive tape 8 is wrapped on the closed annular slot 7 formed by piston 23, piston chamber 22 and the rubber band 24. There opens a small hole 54 on the plugboard 53, and there also left a corresponding window 55 on the self-adhesive film 51 outmost of the urine cup 100. Before detection occurs, no green self-adhesive tape 8 can be seen from the window 55 and the small hole 54, while after the detection is activated, the piston 23 is driven to the corresponding position by the driving handle 60, the liquid specimen transfers, and the green self-adhesive tape 8 also moves along with the piston 23. When the green self-adhesive tape 8 can be seen from the above small hole 54 and the window 55, it means that liquid specimen has been transferred from the transferring chamber 22 to the detecting chamber 32, and the detection is activated.

Figure 4:
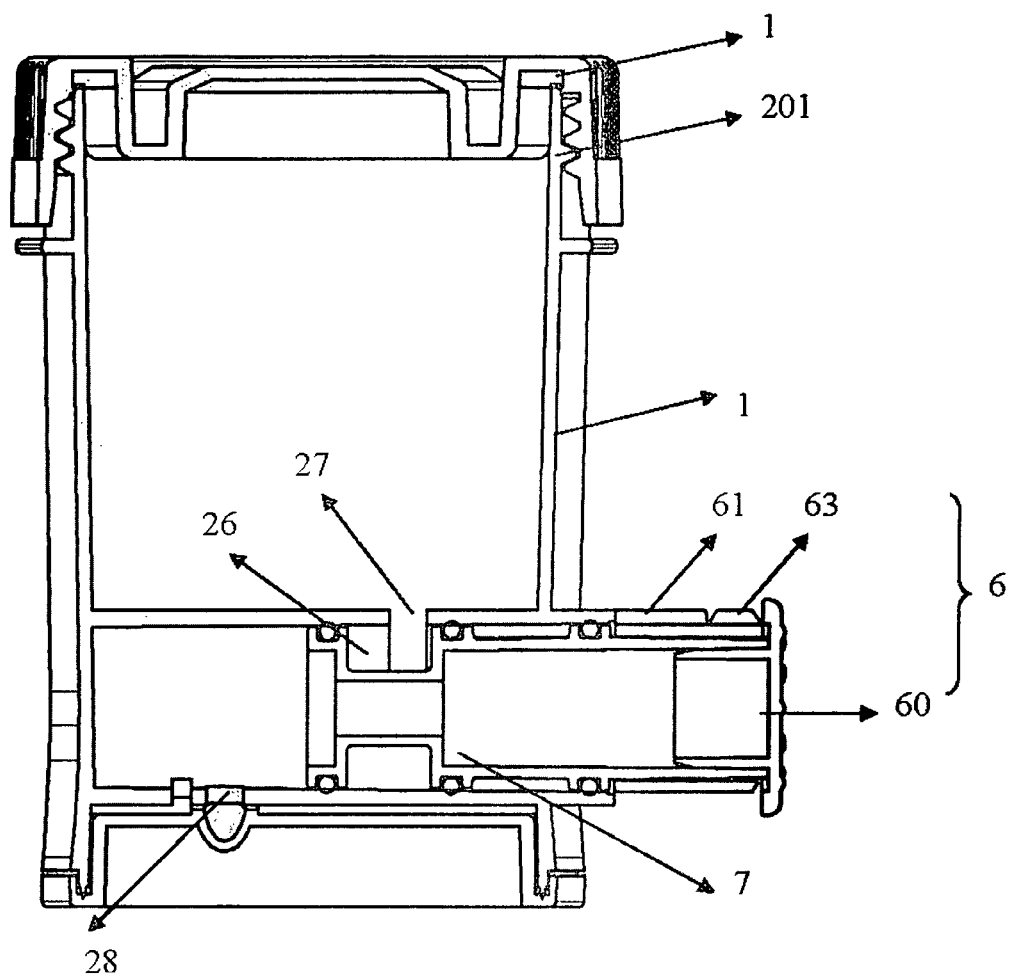
FIG. 4 is a cross sectional view of a specific example of the invention prior to detecting.
Figure 5:
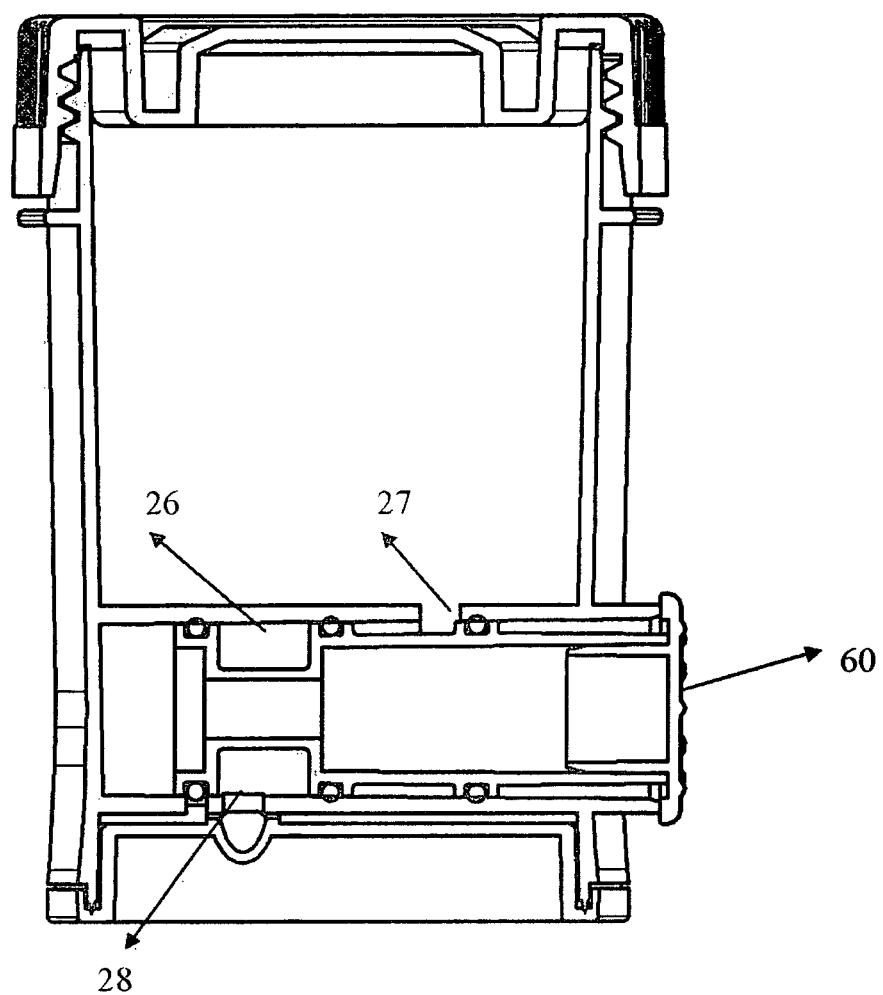
FIG. 5 is a cross sectional view of a specific example of the invention during and after detection.

As shown in FIGS. 4 and 5, when the piston is at the first position, the opened annular slot 26 is positioned aiming at the upper through hole 27. When in use, taking off the cup lid 1, adding liquid specimen such as urine to the cup chamber, the liquid specimen flows to the hollow chamber formed by the opened annular slot 26 from the upper through hole 27. Tearing off the blocking loops 61 and 63 from the piston 23 by using the handle 62, then pushing the driving handle 60 to drive the piston 23 into deep of the piston chamber 22 till the opened annular slot 26 is positioned aiming at the lower through hole 28. Then the liquid specimen flows into the transverse slot of the cup seat 3 from the lower through hole 28, then flows into the slot 34 from the transverse slot to contact with the detection strip 52 inserted on the slot 34 to activate the detecting. When the opened annular slot 26 is aimed at the lower through hole 28, the closed annular slot 7 is aimed at the small hole 54 on the plugboard 53; accordingly, the green self-adhesive signal can be seen clearly through the window 55 on the panel of the urine cup and the small hole 54 of the test card, indicating that the detection is activated. When it needs to further confirm the detection, the liquid specimen in the cup chamber can be send to a lab for further detection by professionals.

The invention claimed is:

1. A detection device, comprising:
a) a detecting chamber containing a detecting element analyzing whether a specimen contains an analyte;
b) an indicating element for displaying whether detection is activated;
c) a sample collecting chamber;
d) a transferring chamber for transferring a liquid specimen to the detecting chamber from the sample collecting chamber, the transferring chamber being disposed between the collecting chamber and the detecting chamber;
e) a piston slidably disposed within the transferring chamber, the piston forming an open annular slot configured to receive the liquid specimen, and a closed annular slot disposing the indicating element;

wherein the piston is laterally and non-rotatably movable along the length of the transferring chamber from a first position to a second position,
wherein when in the first position, the open annular slot is in fluid communication with the sample collecting chamber and when in the second position, the open annular slot is in fluid communication with the detecting chamber,
wherein the open annular slot and the closed annular slot move together between the first position and the second position, the indicating element configured to signal transfer of the liquid specimen from the sample collecting chamber to the detecting chamber and activation of detection, and
wherein the detection device further comprises a driving element for flowing the liquid specimen from the transferring chamber to the detecting chamber, the driving element being in operable connection with the piston and a blocking element, the blocking element being connected with a terminal handle of the driving element as one piece and being operable to prevent lateral movement of the piston from the first position when the blocking element is in a first configuration and operable to allow movement of the piston from the first position to the second position when the blocking element is in a second configuration.

2. The detection device according to claim 1, wherein the detection device further comprises an observation window for observing whether the detection is activated.

3. The detection device according to claim 2, wherein the indicating element is not visible from the observation window before the detection is activated, and is visible from the observation window after the detection is activated.

4. The detection device according to claim 1, wherein the indicating element comprises a colored self-adhesive tape.

5. The detection device according to claim 1, wherein the detecting chamber comprises a test card having a through hole through which the indicating element can be visible after the detection is activated.

6. The detection device according to claim 1, wherein the blocking element can be easily peeled off from the driving element.

7. The detection device according to claim 6, wherein the blocking element comprises a handle to facilitate its peeling off from the driving element.

8. The detection device according to claim 1, wherein activation of flowing the liquid specimen from the transferring chamber to the detecting chamber by the driving element is irreversible.

9. The detection device according to claim 1, wherein the detecting chamber further comprises a support element for supporting the detecting element.

10. A detection device, comprising:
a) a sample collecting chamber;
b) a detecting chamber;
c) a transferring chamber for transferring liquid specimen to the detecting chamber from the sample collecting chamber;
d) a driving element for activating the liquid specimen flow from the transferring chamber to the detecting chamber, the driving element having a blocking element connected with a terminal handle of the driving element as one piece before the detection is activated;
e) an indicating element; and
f) a piston slidably disposed in the transferring chamber, the piston forming an open annular slot configured to receive the liquid specimen, and a closed annular slot disposing the indicating element;

wherein the piston is laterally and non-rotatably movable along the length of the transferring chamber from a first position prior to activation, to a second position, wherein when in the first position, the open annular slot is in fluid communication with the sample collecting chamber and when in the second position, the open annular slot is in fluid communication with the detecting chamber;

wherein the open annular slot and the closed annular slot move together between the first position and the second position, the indicating element configured to signal transfer of the liquid specimen from the sample collecting chamber to the detecting chamber and activation of detection, and wherein the driving element is in operable connection with the piston, and wherein the blocking element is operable to prevent lateral movement of the piston from the first position when the blocking element is connected to the piston and operable to allow movement of the piston from the first position to the second position when the blocking element is detached from the piston.

11. The detection device according to claim 10, wherein the blocking element can be easily peeled off from the driving element.

12. The detection device according to claim 11, wherein the blocking element comprises a handle to facilitate its peeling off from the driving element.

13. The detection device according to claim 10, wherein activation of the liquid specimen flow from the transferring chamber to the detecting chamber by the driving element is irreversible.

14. The detection device according to claim 10, wherein the detecting chamber further comprises a detecting element, and a support element for supporting the detecting element.

15. The detection device according to claim 1, wherein the materials of which the driving element is made comprises plastics.

* * * * *